United States Patent [19]
Ali

[11] Patent Number: 5,900,422
[45] Date of Patent: May 4, 1999

[54] FIBRINOGEN RECEPTOR ANTAGONISTS

[75] Inventor: Fadia El-Fehail Ali, Cherry Hill, N.J.

[73] Assignee: SmithKline Beecham Corporation, Philadelphia, Pa.

[21] Appl. No.: 08/875,358

[22] PCT Filed: Dec. 22, 1995

[86] PCT No.: PCT/US95/16960

§ 371 Date: Jun. 20, 1997

§ 102(e) Date: Jun. 20, 1997

[87] PCT Pub. No.: WO96/19221

PCT Pub. Date: Jun. 27, 1996

Related U.S. Application Data

[63] Continuation of application No. 08/363,160, Dec. 22, 1994, abandoned.

[51] Int. Cl.$^6$ ...................... A61K 31/445; A61K 31/495; C07D 401/10; C07D 401/14

[52] U.S. Cl. .............................................. 514/316

[58] Field of Search ..................... 544/360, 364; 546/186, 187, 193; 514/255, 316, 318

[56] References Cited

U.S. PATENT DOCUMENTS

| | | | |
|---|---|---|---|
| 4,568,543 | 2/1986 | Borrelli et al. | 424/94.62 |
| 5,039,805 | 8/1991 | Alig et al. | 546/224 |
| 5,220,050 | 6/1993 | Bovy et al. | 514/357 |
| 5,756,519 | 5/1998 | Bondinell et al. | 514/316 |

FOREIGN PATENT DOCUMENTS

WO 96/19223  6/1996  WIPO.

OTHER PUBLICATIONS

J. Med. Chem; G.D. Hartman, et al., vol. 25, No. 24, issued 1992, "Non–Peptide Receptor Antagonists", pp. 4606–4642.
Science; E. Ruoslahti, et al., vol. 238, issued Oct. 1987, "New Perspectives in Cell Adhesions: RGD and Integrins", pp. 492–496.

*Primary Examiner*—Ceila Chang
*Attorney, Agent, or Firm*—Zoltan Kerekes; Charles M. Kinzig; Stephen Venetianer

[57] ABSTRACT

This invention relates to compounds of the formula:

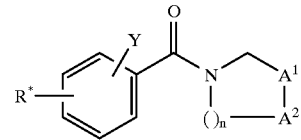

which are effective for inhibiting platelet aggregation, pharmaceutical compositions for effecting such activity, and a method for inhibiting platelet aggregation.

6 Claims, No Drawings

FIBRINOGEN RECEPTOR ANTAGONISTS

This application is a 371 of PCT/US95/16960 filed Dec. 22, 1995, which is a continuation of Ser. No. 08/363,160 filed Dec. 22, 1994 now abandoned.

FIELD OF THE INVENTION

This invention relates to novel compounds which inhibit platelet aggregation, pharmaceutical compositions containing the compounds and methods of using the compounds.

BACKGROUND OF THE INVENTION

Platelet aggregation is believed to be mediated primarily through the fibrinogen receptor, or GPIIb-IIIa platelet receptor complex, which is a member of a family of adhesion receptors referred to as integrins. It has been found that frequently the natural ligands of integrin receptors are proteins which contain an Arg-Gly-Asp sequence. Von Willebrand factor and fibrinogen, which are considered to be natural ligands for the GPIIb-IIIa receptor, possess an Arg-Gly-Asp (RGD in single letter amino acid code) sequence in their primary structure. Functionally, these proteins are able to bind and crosslink GPIIb-IIIa receptors on adjacent platelets and thereby effect aggregation of platelets.

Fibronectin, vitronectin and thrombospondin are RGD-containing proteins which have also been demonstrated to bind to GPIIb-IIIa. Fibronectin is found in plasma and as a structural protein in the intracellular matrix. Binding between the structural proteins and GPIIb-IIIa may function to cause platelets to adhere to damaged vessel walls.

Linear and cyclic peptides which bind to vitronectin and contain an RGD sequence are disclosed in WO 89/05150 (PCT US88/04403). EP 0 275 748 discloses linear tetra- to hexapeptides and cyclic hexa- to octapeptides which bind to the GPIIb-IIIa receptor and inhibit platelet aggregation. Other linear and cyclic peptides, the disclosure of which are incorporated herein by reference, are reported in EP-A 0 341 915. However, the peptide like structures of such inhibitors often pose problems, such as in drug delivery, metabolic stability and selectivity. Inhibitors of the fibrinogen receptor which are not constructed of natural amino acid sequences are disclosed in EP-A 0 372,486, EP-A 0 381 033 and EP-A 0 478 363. WO 92/07568 (PCT/US91/08166) discloses fibrinogen receptor antagonists which mimic a conformational γ-turn in the RGD sequence by forming a monocyclic seven-membered ring structure. There remains a need, however, for novel fibrinogen receptor antagonists (e.g., inhibitors of the GPIIb-IIIa protein) which have potent in vivo and in vitro effects and lack the peptide backbone structure of amino acid sequences.

The present invention discloses novel compounds. These compounds inhibit the GPIIb-IIIa receptor and inhibit platelet aggregation.

SUMMARY OF THE INVENTION

In one aspect this invention is a compound as described hereinafter in formula (I).

This invention is also a pharmaceutical composition for inhibiting platelet aggregation or clot formation, which comprises a compound of formula (I) and a pharmaceutically acceptable carrier.

This invention is further a method for inhibiting platelet aggregation in a mammal in need thereof, which comprises internally administering an effective amount of a compound of formula (I).

In another aspect, this invention provides a method for inhibiting reocclusion of an artery or vein in a mammal following fibrinolytic therapy, which comprises internally administering an effective amount of a fibrinolytic agent and a compound of formula (I). This invention is also a method for treating stroke, transient ischemia attacks, or myocardial infarction.

DETAILED DESCRIPTION OF THE INVENTION

This invention discloses compounds which inhibit platelet aggregation. The compounds of the instant invention are believed to interact favorably with the GPIIb-IIIa receptor.

Although not intending to be bound to any specific mechanism of action, these compounds are believed to inhibit the binding of fibrinogen to the platelet-bound fibrinogen receptor GPIIb-IIIa, and may interact with other adhesion proteins via antagonism of a putative RGD binding site.

The compounds of this invention are compounds of formula (I):

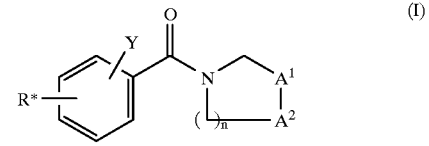

wherein:

$A^1$ is $CH_2$ or $CHR^1$ and $A^2$ is $CH_2$, $CHR^1$, or $NR^2$, with the proviso that $A^1$ or $A^2$ are not simultaneously $CH_2$;

Y is hydrogen, $C_{1-6}$alkyl, halo, $CF_3$, $CH_2OR^4$, $COR^4$, $CONR^4R^4$, $CO_2R^4$, CN, aryl, heteroaryl, $NR^4R^4$, $NR^4COR^4$, $NR^4CO_2R^4$, $NR^4CONR^4R^4$, $NR^4SO_2R^4$, $NO_2$, $OR^4$, $S(O)_{0-2}R^4$, or $SO_{(0-2)}CF_3$;

$R^1$ is $-(CH_2)_m COR^3$;

$R^2$ is $-(CH_2)_q COR^3$;

R* is

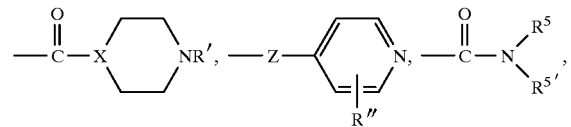

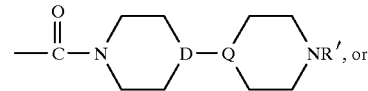

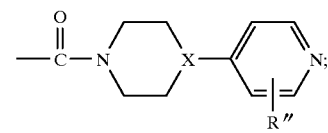

$R^3$ is OR' or NR'R';

$R^4$ is hydrogen, $C_{1-6}$alkyl, aralkyl$C_{1-6}$, aryl, heteroaralkyl$C_{1-6}$, or heteroaryl;

each R' independently is hydrogen or $C_{1-6}$alkyl;

R" is hydrogen, $C_{1-6}$alkyl, or NR'R';

D and Q independently are CH or N, with the proviso that D and Q are not simultaneously N;

X is CH or N;

Z is C(O)NR' or NR'C(O);

R$^5$ and R$^{5'}$ independently are —(CH$_2$)$_s$—Ⓝ;

Ⓝ is piperidine, piperazine, or 2-, 3-, or 4-pyridine;

m is 0–3;

n is 0–3;

each q independently is 1–3; and s is 1–4;

or a pharmaceutically acceptable salt thereof.

Also included in this invention are pharmaceutically acceptable addition salts, complexes or prodrugs of the compounds of this invention. Prodrugs are considered to be any covalently bonded carriers which release the active parent drug according to formula (I) in vivo.

In cases wherein the compounds of this invention may have one or more chiral centers, unless specified, this invention includes each unique nonracemic compound which may be synthesized and resolved by conventional techniques. In cases in which the compounds have unsaturated double bonds, both the cis (Z) and trans (E) are within the scope of this invention. The meaning of any substituent at any one occurrence is independent of its meaning, or any other substituent's meaning, at any other occurrence, unless specified otherwise.

Suitably, the compounds of formula (I) are those wherein R* is

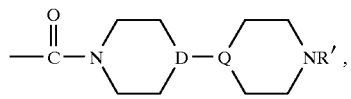

in which R$^3$ is OR', D and Q are each CH, and n is 1 or 2.

Preferred compounds of this invention are:

1-[4,4'-bipiperidin-1-yl]isophthalyl-4-piperidine carboxylic acid;

(+)-1-[4,4'-bipiperidin-1-yl]isophthalyl-3-piperidine carboxylic acid;

1-[4,4'-bipiperidin-1-yl]terephthalyl-4-piperidine carboxylic acid; and (+)-1-[4,4'-bipiperidin-1-yl]terephthalyl-3-piperidine carboxylic acid; or pharmaceutically acceptable salts thereof.

In the above description, C$_{1-6}$alkyl is meant to include methyl, ethyl, n-propyl, isopropyl, n-butyl, isobutyl, t-butyl, n-pentyl, isopentyl, neopentyl and hexyl and the simple aliphatic isomers thereof.

C$_{2-6}$ alkenyl as applied herein means an alkyl group of 2 to 6 carbons wherein a carbon-carbon single bond is replaced by a carbon-carbon double bond. C$_{2-6}$alkenyl includes ethylene, 1-propene, 2-propene, 1-butene, 2-butene, isobutene and the several isomeric pentenes and hexenes. Both cis and trans isomers are included.

C$_{2-6}$ alkynyl means an alkyl group of 2 to 6 carbons wherein one carbon-carbon single bond is replaced by a carbon-carbon triple bond. C$_{2-6}$ alkynyl includes acetylene, 1-propyne, 2-propyne, 1-butyne, 2-butyne, 3-butyne and the simple isomers of pentyne and hexyne.

Aryl, as applied herein, means phenyl or naphthyl, or phenyl or naphthyl substituted by one to three moieties R$^{11}$. In particular, R$^{11}$ may be C$_{1-4}$alkyl, C$_{1-4}$alkoxy, C$_{1-4}$alkthio, trifluoroalkyl, OH, F, Cl, Br or I. AralkylC$_{1-6}$, as used herein, means an aryl group attached to a C$_{1-6}$alkyl chain.

Heteroaryl indicates an optionally substituted five or six membered aromatic monocyclic ring, or a nine or ten-membered bicyclic ring containing one to three heteroatoms chosen from the group of nitrogen, oxygen and sulfur, which are stable and available by conventional chemical synthesis. Illustrative heteroaryls are benzofuryl, benzimidazole, benzothiophene, furan, imidazole, and pyridine. Any accessible combination of up to three substituents, such as chosen from R$^{11}$, on the heteroaryl ring that is available by chemical synthesis and is stable is within the scope of this invention. HeteroaralkylC$_{1-6}$, as used herein, means a heteroaryl group attached to C$_{1-6}$alkyl chain.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to C$_{1-6}$alkyl, Nph refers to 1- or 2-naphthyl and cHex refers to cyclohexyl. MeArg is N α-methyl arginine. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to N-ethyl-N'(dimethylaminopropyl)-carbodiimide. HOBt refers to 1-hydroxybenzotriazole, THF refers to tetrahydrofuran, DMF refers to dimethyl formamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The compounds of formula (I) are generally prepared by reacting a compound of the formula (II) with a compound of the formula (III):

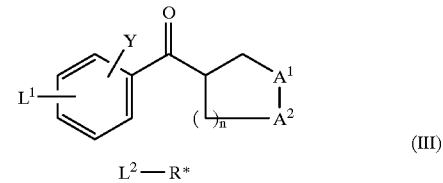

wherein Y, A$^1$, A$^2$, R* and n are as defined in formula (I), with any reactive functional groups protected;

and thereafter removing any protecting groups, and optionally forming a pharmaceutically acceptable salt.

It will be apparent that the precise identity of L$^1$ in formula (II) is a functional group capable of reacting with L$^2$ of formula (III) to form the NCO linkage. For example, L$^1$ may be CO$_2$H and the NCO linkage is obtained by activation of the carboxyl and condensation with (III) to give the desired arnide. Methods for activating a carboxylic acid for condensation with an amide include treatment with a carbodiimide, with thionyl chloride for form an acid chloride, or with acid anhydrides, acid chlorides or chloroformates to form mixed anhydrides.

In another approach, L$^1$ may be bromo, iodo, trifluoromethylsulfonyloxy, etc. and the NCO linkage is formed by palladium-catalyzed aminocarbonylation with of (II) with (III) and carbon monoxide in a suitable solvent such as dimethylformamide, N-methylpyrrolidinone, toluene, etc.

Many additional methods for converting a carboxylic acid to an amide are known, and can be found in the art including standard reference books, such as "Compendium of Organic Synthetic Methods", Vol. I-VI (Wiley-Interscience).

Compounds of formula (I) are prepared by methods analogous to those described in Scheme I.

Scheme I

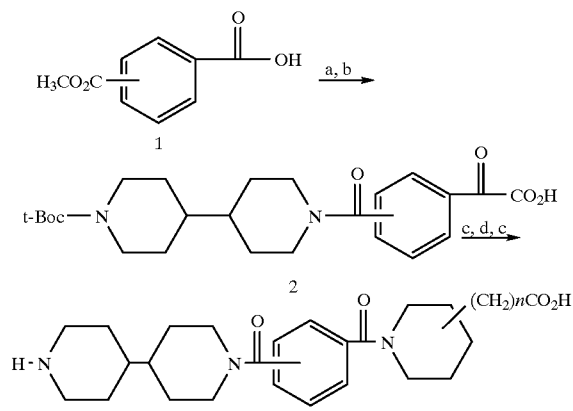

a) Boc-piperidine HCl, EDC, HOBt, DIEA/DMF;
b) 1 N NaOH/MeOH-THF
c) ethyl nipecotate or isonepicotate, EDC, HOBt, DIEA;
d) 20% TFA/CH2Cl2;
d) 1N NaOH/EtOH The monomethylisophthalate (I-1) was condensed with t-Boc-pipiperidine hydrochloride in the presence of DIEA, HOBt. $H_2O$ and EDC in anhydrous DMF. Saponification of the resulting methyl ester with 1N NaOH afforded the monoacid (I-2). Condensation of (I2) with either ethyl isonepicotate or nepicotate in the presence of EDC, HOBt. $H_2O$ and DIEA afforded the fully protected version of (I-3). Removal of the N-protected t-Boc group by 20% TFA in methylene chloride followed by saponification of the ethyl ester with 1N NaOH in ethanol, then neutralization of the basic solution with 50% acetic acid afforded the final product (I3) as a zwetterion.

Coupling reagents as used herein denote reagents which may be used to form amide bonds. Typical coupling methods employ carbodiimides, activated anhydrides and esters and acyl halides. Reagents such as EDC, DCC, DPPA, PPA, BOP reagent, HOBt, N-hydroxysuccinimide and oxalyl chloride are typical.

Coupling methods to form amide bonds are generally well known to the art. The methods of peptide synthesis generally set forth by Bodansky et al., THE PRACTICE OF PEPTIDE SYNTHESIS, Springer-Verlag, Berlin, 1984, Ali et al. in *J. Med. Chem.*, 29, 984 (1986) and *J. Med. Chem.*, 30, 2291 (1987) are generally illustrative of the technique and are incorporated herein by reference.

Solution synthesis for the formation of amide bonds is accomplished using conventional methods used to form amide bonds. Typically, the amine or aniline is coupled via its free amino group to an appropriate carboxylic acis substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran(THF), in the presence of a base, such as N-methyl morpholine, DMAP or a trialkylamine, with isobutyl chloroformate to form the "activated anhydride", which is subsequently reacted with the free amine of a second protected amino acid or aniline.

The reactive functional groups of the sidechains of each synthetic fragment are suitably protected as known in the art. Suitable protective groups are disclosed in Greene, PROTECTIVE GROUPS IN ORGANIC CHEMISTRY, John Wiley and Sons, New York, 1981. For example, the Boc, Cbz, phthaloyl or Fmoc group may be used for protection of an amino or amidino group. The Boc group is generally preferred for protection of an α-amino group. A t-Bu, cHex or benzyl ester may be used for the protection of the side chain carboxyl. A benzyl group or suitably substituted benzyl group (e.g., 4-methoxy-benzyl or 2,4-dimethoxybenzyl) is used to protect the mercapto group or the hydroxyl group. A suitably substituted carbobenzyloxy group or benzyl group may be also be used for the hydroxyl group or amino group. Suitable substitution of the carbobenzyloxy or benzyl protecting groups is ortho and/or para substitution with chloro, bromo, nitro or methyl, and is used to modify the reactivity of the protective group. Except for the Boc group, the protective groups for the amino moiety are, most conveniently, those which are not removed by mild acid treatment. These protective groups are removed by such methods as catalytic hydrogenation, sodium in liquid ammonia or HF treatment, as known in the art.

Acid addition salts of the compounds of this invention are prepared in a standard manner in a suitable solvent from the parent compound and an excess of an acid, such as hydrochloric, hydrobromic, sulfuric, phosphoric, acetic, maleic, succinic or methanesulfonic. The acetate salt form is especially useful. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li+$, $Na+$, $K+$, $Ca++$, $Mg++$ and $NH_4+$ are specific examples of cations present in pharmaceutically acceptable salts.

This invention provides a pharmaceutical composition which comprises a compound according to formula (I) and a pharmaceutically acceptable carrier. Accordingly, the compounds of formula (I) may be used in the manufacture of a medicament. Pharmaceutical compositions of the compounds of formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, the compounds of this invention may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository. The compounds of this invention may be used in vitro to inhibit the aggregation of platelets in blood and blood products, e.g., for storage, or for ex vivo manipulations such as in diagnostic or research use.

This invention also provides a method of inhibiting platelet aggregation and clot formation in a mammal, especially a human, which comprises the internal administration of a compound of formula (I) and a pharmaceutically acceptable carrier. Indications for such therapy include acute myocardial infarction (AMI), deep vein thrombosis, pulmonary embolism, dissecting anurysm, transient ischemia attack (TIA), stroke and other infarct-related disorders, and unstable angina. Chronic or acute states of hyperaggregability, such as disseminated intravascular coagulation (DIC), septicemia, surgical or infectious shock, postoperative and post-partum trauma, cardiopulmonary bypass surgery, incompatible blood transfusion, abruptio placenta, thrombotic thrombocytopenic purpura (TTP), snake venom and immune diseases, are likely to be responsive to such treatment. In addition, the compounds of this invention may be useful in a method for the prevention of metastatic conditions, the prevention or treatment of fungal or bacterial infection, inducing immunostimulation, treatment of sickle cell disease, and the prevention or treatment of diseases in which bone resorption is a factor.

The compounds of formula (I) are administered either orally or parenterally to the patient, in a manner such that the concentration of drug in the plasma is sufficient to inhibit platelet aggregation, or other such indication. The pharmaceutical composition containing the compound is administered at a dose between about 0.2 to about 50 mg/kg in a manner consistent with the condition of the patient. For acute therapy, parenteral administration is preferred. For persistent states of hyperaggregability, an intravenous infusion of the peptide in 5% dextrose in water or normal saline is most effective, although an intramuscular bolus injection may be sufficient.

For chronic, but noncritical, states of platelet aggregability, oral administration of a capsule or tablet, or a bolus intramuscular injection is suitable. The compound of this invention is administered one to four times daily at a level of about 0.4 to about 50 mg/kg to achieve a total daily dose of about 0.4 to about 200 mg/kg/day.

This invention further provides a method for inhibiting the reocclusion of an artery or vein following fibrinolytic therapy, which comprises internal administration of a compound of formula (I) and a fibrinolytic agent. It has been found that administration of an peptide in fibrinolytic therapy either prevents reocclusion completely or prolongs the time to reocclusion.

When used in the context of this invention the term fibrinolytic agent is intended to mean any compound, whether a natural or synthetic product, which directly or indirectly causes the lysis of a fibrin clot. Plasminogen activators are a well known group of fibrinolytic agents. Useful plasminogen activators include, for example, anistreplase, urokinase (UK), pro-urokinase (pUK), streptokinase (SK), tissue plasminogen activator (tPA) and mutants, or variants, thereof, which retain plasminogen activator activity, such as variants which have been chemically modified or in which one or more amino acids have been added, deleted or substituted or in which one or more or functional domains have been added, deleted or altered such as by combining the active site of one plasminogen activator with the fibrin binding domain of another plasminogen activator or fibrin binding molecule. Other illustrative variants include tPA molecules in which one or more glycosylation sites have been altered. Preferred among plasminogen activators are variants of tPA in which the primary amino acid sequence has been altered in the growth factor domain so as to increase the serum half-life of the plasminogen activator. tPA Growth factor variants are disclosed, e.g., by Robinson et al., EP-A 0 297 589 and Browne et al., EP-A 0 240 334. Other variants include hybrid proteins, such as those disclosed in EP 0 028 489, EP 0 155 387 and EP 0 297 882, all of which are incorporated herein by reference. Anistreplase is a preferred hybrid protein for use in this invention. Fibrinolytic agents may be isolated from natural sources, but are commonly produced by traditional methods of genetic engineering.

Useful formulations of tPA, SK, UK and pUK are disclosed, for example, in EP-A 0 211 592, EP-A 0 092 182 and U.S. Pat. No. 4,568,543, all of which are incorporated herein by reference. Typically the fibrinolytic agent may be formulated in an aqueous, buffered, isotonic solution, such as sodium or ammonium acetate or adipate buffered at pH 3.5 to 5.5. Additional excipients such as polyvinyl pyrrolidone, gelatin, hydroxy cellulose, acacia, polyethylene, glycol, mannitol and sodium chloride may also be added. Such a composition can be lyophilized.

The pharmaceutical composition may be formulated with both the compound of formula (I) and fibrinolytic in the same container, but formulation in different containers is preferred. When both agents are provided in solution form they can be contained in an infusion/injection system for simultaneous administration or in a tandem arrangement.

Indications for such therapy include myocardial infarction, deep vein thrombosis, pulmonary embolism, stroke and other infarct-related disorders. The compound of formula (I) is administered just prior to, at the same time as, or just after parenteral administration of tPA or other fibrinolytic agent. It may prove desirable to continue treatment with the peptide for a period of time well after reperfusion has been established to maximally inhibit post-therapy reocclusion. The effective dose of tPA, SK, UK or pUK may be from 0.5 to 5 mg/kg and the effective dose of the compound of this invention may be from about 0.1 to 25 mg/kg.

For convenient administration of the inhibitor and the fibrinolytic agent at the same or different times, a kit is prepared, comprising, in a single container, such as a box, carton or other container, individual bottles, bags, vials or other containers each having an effective amount of the inhibitor for parenteral administration, as described above, and an effective amount of tPA, or other fibrinolytic agent, for parenteral administration, as described above. Such kit can comprise, for example, both pharmaceutical agents in separate containers or the same container, optionally as lyophilized plugs, and containers of solutions for reconstitution. A variation of this is to include the solution for reconstitution and the lyophilized plug in two chambers of a single container, which can be caused to admix prior to use. With such an arrangement, the fibrinolytic and the compound of this invention may be packaged separately, as in two containers, or lyophilized together as a powder and provided in a single container.

When both agents are provided in solution form, they can be contained in an infusion/injection system for simultaneous administration or in a tandem arrangement. For example, the platelet aggregation inhibitor may be in an i.v. injectable form, or infusion bag linked in series, via tubing, to the fibrinolytic agent in a second infusion bag. Using such a system, a patient can receive an initial bolus-type injection or infusion, of the peptide inhibitor followed by an infusion of the fibrinolytic agent.

The pharmacological activity of the compounds of this invention is assessed by their ability to inhibit the binding of $^3$H-SK&F 107260, a known RGD-fibrinogen antagonist, to the GPIIbIIIa receptor; their ability to inhibit platelet aggregation, in vitro, and their ability to inhibit thrombus formation in vivo.

Inhibition of RGD-mediated GPIIb-IIIa binding
Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mnM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb-IIIa was eluted with buffer A containing 10% dextrose. All procedures were performed at 4° C. The GPIIb-IIIa obtained was >95% pure as shown by SDS polyacrylamide gel electrophoresis.
Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes wee centrifuged at 12,000g for 15 min and resuspended in the dialysis buffer at a final protein concentration of approximately 1 mg/mL. The liposomes were stored at –70° C. until needed.
Competitive Binding to GPIIb-IIIa The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 μg/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 μg of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 μM unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: Ki=IC50/(1+L/Kd), where L is the concentration of [3H]-SK&F-107260 used in the competitive binding assay (4.5 nM), and Kd is the dissociation constant of [3H]-SK&F-107260 which is 4.5 nM as determined by Scatchard analysis. The compounds of this invention inhibit [3H]-SK&F-107260 binding with a Ki in the range of about 2.0 micromolar to about 20.0 micromolar.

Inhibition of Platelet Aggregation

Inhibition of platelet aggregation was determined following the procedure described in Nichols, et al., *Thrombosis Research*, 75, 143 (1994). Blood was drawn from the antecubital vein of normal human volunteers who had not taken a cyclooxygenase inhibitor within the previous 14 days into a plastic syringe containing one part 3.8% trisodium citrate to nine parts blood. Platelet rich plasma was prepared by centrifuging the blood at 200 g for 10 min at RT. The platelet rich plasma was drawn off and the remaining blood was centrifuged at 2400 g for 5 min at RT to make platelet poor plasma. Platelet count was measured with a model ZB 1 Coulter Counter (Coulter Electronics Inc., Hialeah, Fla.) and was adjusted to 300,000/μl using platelet poor plasma. Platelet aggregation was studied in a Chrono-Log model 400VS Lumi Aggregometer (Chrono-Log, Havertown, Pa.) using platelet rich plasma stirred at 1200 r.p.m.and maintained at 37° C., with platelet poor plasma as the 100% transmission standard. Concentration-response curves for the ability of compounds to inhibit platelet aggregation, measured as the maximum change in light transmission, induced by a maximal concentration of adenosine diphosphate (10 μM) were constructed and the $IC_{50}$ was determined as the concentration of antagonist required to produce 50% inhibition of the response to the agonist.

In Vivo Inhibition of Platelet Aggregation

In vivo inhibition of thrombus formation is demonstrated by recording the systemic and hemodynamic effects of infusion of the peptides into anesthetized dogs according to the methods described in Aiken et al., *Prostaglandins*, 19, 629 (1980).

The examples which follow are intended to in no way limit the scope of this invention, but are provided to illustrate how to make and use the compounds of this invention. Many other embodiments will be readily apparent and available to those skilled in the art.

General

Nuclear magnetic resonance spectra were recorded at 400 MHz using a Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC were carried out on Rainin or Beckman chromatographs. ODS refers to an octadecylsilyl derivatized silica gel chromatographic support. 5 μ Apex-ODS indicates an octadecylsilyl derivatized silica gel chromatographic support having a nominal particle size of 5 μ, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

Monomethyl isophthalate, monomethylterephthalate, tert-butyl-β-alanine hydrochloride and t-butyl glycinate hydrochloride were purchased from Aldrich, Lancaster chemicals or Bachem, 4-pyridyl piperazine was purchased from EMKCHEMIE GMBH and N-(tert-butoxycarbonyl)-4,4'-bipiperidine was prepared by the method of Bondinell, et al., WO 94/14776.

EXAMPLE 1

Preparation of Preparation of 1-[4,4'-Bipiperidin-1-yl]isophthalyl-4-piperidine carboxylic acid a) Methyl [N-(tert-butoxycarbonyl)-4,4'-bipiperidin-1-yl] isophthalate (EDC) (1.25 g, 6.5 mmol) was added to a solution of monomethyl isophthalate (0.9 g, 5 mmol), N-(tert-butoxycarbonyl)-4,4-bipiperidine hydrochloride (1.53 g, 5 mmol), HOBt. $H_2O$ (0.88 g, 6.5 mmol) and DIEA (1.75 mL, 10 mmol) in anhydrous DMF (25 mnL) at RT. After stirring for 20 h, the reaction was concentrated on rotavap (high vacuum). The yellow oily residue was taken into EtOAc (100 mL) and washed successively with $H_2O$ (3×30 mL), 5% citric acid (3×30 ml), $H_2O$ (3×30 mL), 10% $Na_2CO_3$ (2×30 mL), $H_2O$(3×30 mL) and finally once with saturated salt solution (NaCl). The organic extract was dried (anhydrous $Na_2SO_4$), filtered and concentrated to yield the title compound (2.0 g, 93%) as a white waxy material. HPLC k' 12.7 (Ultrasphere® ODS, gradient, A:acetonitrile B:water-0.1% trifluoroacetic acid, 5–60% acetonitrile during 20 min; UV detection at 220 nm). $^1$H NMR (400 MHz, $CDCl_3$) δ 8.08 (m, 1 H), 7.6 (m, 1 H), 7.4 (m, 1 H), 7.3 (s, 1 H), 3.94 (s, 3 H), 2.6 (m, 2 H), 1.65–1.1 (m, 16 H), 1.47 (s, 9 H). MS (ES) m/e 431.4 [M+H]$^+$.

b) [N-(tert-butoxycarbonyl)-4,4'-bipiperidin-1-yl]isophthalic acid

A solution of 1N NaOH (7 mL, 7 mmol) was added dropwise to a solution of the compound of Example 4 (a) (2.0 g, 4.65 mmol) in a 1:1 mixture of methanoltetrahydrofuran (30 mL). The resulting solution was stirred at RT for 20 h. It was then concentrated, and the resulting oily residue was dissolved in $H_2O$ (30 mL) and acidified upon cooling with 50% acetic acid to acidic pH (5.0). The aqueous solution was then extracted with EtOAc, dried (anhydrous $Na_2SO_4$), filtered and concentrated to yield the title compound (1.73 g, 89%) as a white fluffy powder. HPLC k' 10.9 (Ultrasphere® ODS, gradient, A:acetonitrile B:water-0.1% trifluoroacetic acid, 5–60% acetonitrile during 20 min; UV detection at 220 nm). MS (ES) m/e 417.2 [M+H]$^+$.

c) Ethyl N-[(tert-butoxycarbonyl)-4,4'-bipiperidinyl] isophthalyl-4-piperidine carboxylate EDC (234 mg, 1.2 mmol) was added to a solution of the compound of Example 1 (b) (512 mg, 1.2 mmol), ethyl-4-piperidine carboxylate (191 μL, 1.2 mmol), HOBt. $H_2O$ (165 mg, 1.2 mmol) and DIEA (213 μL, 1.2 mmol) in anhydrous DMF (7 mL) at RT. After stirring for 20 h, the reaction was concentrated on rotavap (high vacuum). The resulting residue was taken into EtOAc and washed successively with $H_2O$ (3×20 mL), 5% citric acid (3×20 ml ), $H_2O$, 10% $Na_2CO_3$ (3×20 ml) and saturated NaCl. The organic extract was dried (anhydrous $Na_2SO_4$), filtered and concentrated to yield the title compound (700 mg, 100%) as a white solid. HPLC k' 12.25 (Ultrasphere® ODS, gradient, A:acetonitrile B:water-0.1% trifluoroacetic acid, 5–60% acetonitrile during 20 min; UV detection at 220 nm). MS (ES) m/e 556.4 [M+H]$^+$.

d) Ethyl N-[4,4'-Bipiperidin-1-yl]isophthalyl-4-piperidine carboxylate

To a solution of the compound of Example 1 (c) (660 mg, 1.2 mmol) in $CH_2Cl_2$ (5 ml) was added trifluoroacetic acid (TFA) (1 ml) at Rt. The resulting mixture was stirred for 6h, then it was concentrated to dryness on rotavap. The resulting oily residue has a MS (ES) m/e 456.2 [M+H]$^+$.

e) N-[4,4'-Bipiperidin-1-yl]isophthalyl-4-piperidine carboxylic acid

To a solution of the compound of Example 1 (d) in ethanol (10 mL) was added a solution of 1N NaOH (6.2 mL, 6.2 mmol) and was stirred at RT for 20 h. It was then concentrated, and the resulting oily residue was dissolved in $H_2O$, and the pH was adjusted to 7 by means of 50% acetic acid. The aqueous solution was purified on flash ODS column (step gradient, 6–9% acetonitrile/water. The fractions containing the pure compound were collected, concentrated and lyophilized to yield the title compound (248 mg, 48% ) as a white powder. HPLC k' 5.8 (Ultrasphere® ODS, gradient, A:acetonitrile B:water-0.1% trifluoroacetic acid, 5–60% acetonitrile during 20 min; UV detection at 220 nm). MS (ES) m/e 428.2 [M+H]$^+$;

Anal. ($C_{24}H_{33}N_3O_4$. 2.5 $H_2O$) calcd: C, 61.00; H, 8.11; N, 8.89. Found: C, 61.27; H, 8.09; N, 8.72.

EXAMPLE 2

Preparation of (+)-1-[4,4'-Bipiperidin-1-yl] isophthalyl-3-piperidine carboxylic acid a) (±) Ethyl N-[(tert-butoxycarbonyl)-4,4'-bipiperidinyl] isophthalyl-3-piperidine carboxylate EDC (234 mg, 1.2 mmol) was added to a solution of the compound of Example 1 (b) (500 mg, 1.2 mmol), (±) ethyl-3-piperidine carboxylate (191 μL, 1.2 mmol), HOBt. $H_2O$ (165 mg, 1.2 mmol) and DIEA (213 μL, 1.2 mmol) in anhydrous DMF (10 mL) at RT. After stirring for 20 h, the reaction was concentrated on rotavap (high vacuum). The resulting residue was taken into EtOAc and washed successively with $H_2O$ (3×20 mL), 5% citric acid (3×20 ml), $H_2O$, 10% $Na_2CO_3$ (3×20 ml) and saturated NaCl. The organic extract was dried (anhydrous $Na_2SO_4$), filtered and concentrated to yield the title compound (500 m g, 75%) as a white solid. HPLC k' 12.54 (Ultrasphere® ODS, gradient, A:acetonitrile B:water-0.1% trifluoroacetic acid, 5–60% acetonitrile during 20 min; UV detection at 220 nm). MS (ES) m/e 556.4 $[M+H]^+$.

b) (±) Ethyl N-[4,4'-Bipiperidin-1-yl]isophthalyl-3-piperidine carboxylate

To a solution of the compound of Example 2 (a) (500 mg, 0.89 mmol) in $CH_2Cl_2$ (8 ml) was added trifluoroacetic acid (TFA) (2 ml) at Rt. The resulting mixture was stirred for 2h, then it was concentrated to dryness on rotavap. The resulting oily residue has a MS (ES) m/e 456.5 $[M+H]^+$.

c) (±) N-[4,4'-Bipiperidin-1-yl]isophthalyl-3-piperidine carboxylic acid

To a solution of the compound of Example 2 (b) in ethanol (10 mL) was added a solution of 1N NaOH (6.0 mL, 6.0 mmol) and was stirred at RT for 20 h. It was then concentrated, and the resulting oily residue was dissolved in $H_2O$, and the pH was adjusted to 6.8 by means of 50% acetic acid. The aqueous solution was purified on flash ODS column (step gradient, 4–10% acetonitrile/water. The fractions containing the pure compound were collected, concentrated and lyophilized to yield the title compound (175 mg, 46% ) as a white powder. HPLC k' 5.87 (Ultrasphere® ODS, gradient, A:acetonitrile B:water-0.1% trifluoroacetic acid, 5–60% acetonitrile during 20 min; UV detection at 220 nm). MS (ES) m/e 428.6 $[M+H]^+$;

Anal. ($C_{24}H_{33}N_3O_4 \cdot H_2O$) calcd: C, 64.70; H, 7.92; N, 9.43. Found: C, 64.61; H, 7.85; N, 9.41.

EXAMPLE 3

Preparation of 1-[4,4'-Bipiperidin-1-yl]terephthalyl-4-piperidine carboxylic acid a) Methyl [N-(tert-butoxycarbonyl)-4,4'-bipiperidin-1-yl] terephthalate (EDC) (2.5 g, 13 mmol) was added to a solution of monomethyl terphthalate (1.8 g, 10 mmol), N-(tert-butoxycarbonyl)-4,4-bipiperidine hydrochloride (3.06 g, 10 mmol), HOBt. $H_2O$ (1.76 g, 13 mmol) and DIEA (3.5 mL, 20 mmol) in anhydrous DMF (50 mL) at RT. After stirring for 20 h, the reaction was concentrated on rotavap (high vacuum). The yellow oily residue was taken into EtOAc (100 mL) and washed successively with $H_2O$ (3×30 mL) , 5% citric acid (3×30 ml), $H_2O$ (3×30 mL), 10% $Na_2CO_3$ (2×30 mL), $H_2O$ (3×30 mL) and finally once with saturated salt solution (NaCl). The organic extract was dried (anhydrous $Na_2SO_4$), filtered and concentrated to yield the title compound (4.2 g, 98%) as a white solid. HPLC k' 12.72 (Ultrasphere® ODS, gradient, A:acetonitrile B:water-0.1% trifluoroacetic acid, 5–60% acetonitiile during 20 min; UV detection at 220 nm). MS (ES) m/e 431.2 $[M+H]^+$.

b) [N-(tert-butoxycarbonyl)-4,4'-bipiperidin -1-yl] terephthalic acid

A solution of 1N NaOH (14 mL, 14 mmol) was added dropwise to a solution of the compound of Example 3 (a) (4.0 g, 9.2 mmol) in a 1:1 mixture of methanoltetrahydrofuran (60 mL). The resulting solution was stirred at RT for 20 h. It was then concentrated, and the resulting oily residue was dissolved in $H_2O$ (60 mL) and acidified upon cooling with 50% acetic acid to acidic pH (5.5). The aqueous solution was then extracted with EtOAc, dried (anhydrous $Na_2SO_4$), filtered and concentrated to yield the title compound (3.73 g, 89%) as a white fluffy powder. HPLC k' 10.86 (Ultrasphere® ODS, gradient, A:acetonitrile B:water-0. 1% trifluoroacetic acid, 5–60% acetonitrile during 20 min; UV detection at 220 nm). MS (ES) m/e 417.2 $[M+H]^+$.

c) Ethyl N-[(tert-butoxycarbonyl)-4,4'-bipiperidinyl] terephthalyl-4-piperidine carboxylate EDC (383 mg, 2.0 mmol) was added to a solution of the compound of Example 3 (b) (840 mg, 2 mmol), ethyl-4-piperidine carboxylate (310 mg, 2 mmol), HOBt $H_2O$ (270 mg, 2 mmol) and DIEA (258 µL, 2 mmol) in anhydrous DMF (10 mL) at RT. After stirring for 20 h, the reaction was concentrated on rotavap (high vacuum). The resulting residue was taken into EtOAc and washed successively with $H_2O$ (3×20 mL), 5% citric acid (3×20 ml ), $H_2O$, 10% $Na_2CO_3$ (3×20 ml) and saturated NaCl. The organic extract was dried (anhydrous $Na_2SO_4$), filtered and concentrated to yield the title compound (1.1 g, 100%) as a white solid. HPLC k' 12.2 (Ultrasphere® ODS, gradient, A:acetonitrile B:water-0.1% trifluoroacetic acid, 5–60% acetonitrile during 20 min; UV detection at 220 nm). MS (ES) m/e 556.4 $[M+H]^+$.

d) Ethyl N-[4,4'-Bipiperidin-1-yl]terephthalyl-4-piperidine carboxylate

To a solution of the compound of Example 3 (c) (1.1 g, 2 mmol) in $CH_2Cl_2$ (16 ml) was added trifluoroacetic acid (TFA) (4 ml) at Rt. The resulting mixture was stirred for 2h, then it was concentrated to dryness on rotavap. The resulting oily residue has a MS (ES) m/e 456.2 $[M+H]^+$.

e) N-[4,4'-Bipiperidin-1-yl]terephthalyl-4-piperidine carboxylic acid

To a solution of the compound of Example 3 (d) in ethanol (20 mL) was added a solution of 1N NaOH (12 mL, 12 mmol) and was stirred at RT for 20 h. It was then concentrated, and the resulting oily residue was dissolved in $H_2O$, and the pH was adjusted to 7 by means of 50% acetic acid. The aqueous solution was purified on flash ODS column (step gradient, 6–10% acetonitrile/water. The fractions containing the pure compound were collected, concentrated and lyophilized to yield the title compound (620 mg, 75% ) as a white powder. HPLC k' 5.65 (Ultrasphere® ODS, gradient, A:acetonitrile B:water-0.1% trifluoroacetic acid, 5–60% acetonitrile during 20 min; UV detection at 220 nm). MS (ES) m/e 428.2 $[M+H]^+$;

Anal. ($C_{24}H_{33}N_3O_4 \cdot 1.75 H_2O$) calcd: C, 62.71; H, 8.01; N, 9.15. Found: C, 63.02; H, 8.08; N, 9.13.

EXAMPLE 4

Preparation of (±)-1-[4,4'-Bipiperidin-1-yl] terephthalyl-3-piperidine carboxylic acid a) (±) Ethyl N-[(tert-butoxycarbonyl)-4,4'-bipiperidinyl] terephthalyl-3-piperidine carboxylate EDC (383 mg, 2 mmol) was added to a solution of the compound of Example 3 (b) (840 mg, 2 mmol), (±) ethyl-3-piperidine carboxylate (310 µL, 2 mmol), HOBt $H_2O$ (270 mg, 2 mmol) and DIEA (350 µL, 2 mmol) in anhydrous DMF (10 mL) at RT. After stirring for 20 h, the reaction was concentrated on rotavap (high vacuum). The resulting residue was taken into EtOAc and washed successively with $H_2O$ (3×20 mL), 5% citric acid (3×20 ml ), $H_2O$, 10% $Na_2CO_3$ (3×20 ml) and saturated NaCl. The organic extract was dried (anhydrous $Na_2SO_4$), filtered and concentrated to yield the title compound (1.07 m g, 96%) as a white solid. HPLC k' 12.38 (Ultrasphere® ODS, gradient, A:acetonitrile B:water-0.1% trifluoroacetic acid, 5–60% acetonitrile during 20 min; UV detection at 220 nm). MS (ES) m/e 556.4 $[M+H]^+$.

b) (±) Ethyl N-[4,4'-Bipiperidin-1-yl]terephthalyl-3-piperidine carboxylate

To a solution of the compound of Example 4 (a) (1.1 g, 2 mmol) in CH$_2$Cl$_2$ (20 ml) was added trifluoroacetic acid (TFA) (4 ml) at Rt. The resulting mixture was stirred for 2h, then it was concentrated to dryness on rotavap. The resulting oily residue has a MS (ES) m/e 456.2 [M+H]$^+$.

c) (±) N-[4,4'-Bipiperidin-1-yl]terephthalyl-3-piperidine carboxylic acid

To a solution of the compound of Example 4 (b) in ethanol (20 mL) was added a solution of 1N NaOH (10.0 mL, 10.0 mmol) and was stirred at RT for 20 h. It was then concentrated, and the resulting oily residue was dissolved in H$_2$O, and the pH was adjusted to 6.9 by means of 50% acetic acid. The aqueous solution was purified on flash ODS column (step gradient, 4–9% acetonitrile/water. The fractions containing the pure compound were collected, concentrated and lyophilized to yield the title compound (420 mg, 55%) as a white powder. HPLC k' 5.93 (Ultrasphere® ODS, gradient, A:acetonitrile B:water-0.1% trifluoroacetic acid, 5–60% acetonitrile during 20 min; UV detection at 220 nm). MS (ES) m/e 428.2 [M+H]$^+$;

Anal. (C$_{24}$H$_{33}$N$_3$O$_4$. 4 H$_2$O) calcd: C, 57.70; H, 8.27; N, 8.41. Found: C, 57.88; H, 8.18; N, 8.42.

EXAMPLE 5

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

EXAMPLE 6

Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

EXAMPLE 7

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

The foregoing is illustrative of the making and using of this invention. This invention, however, is not limited to the precise embodiments described herein, but encompasses all modifications within the scope of the claims which follow.

What is claimed is:
1. A compound of the formula:

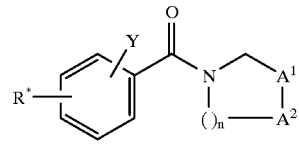

wherein:

$A^1$ is CH$_2$ or CHR$^1$ and $A^2$ is CH$_2$, CHR $^1$, or NR$^2$, with the proviso that $A^1$ or $A^2$ are not simultaneously CH$_2$;

Y is hydrogen, C$_{1-6}$alkyl, halo, CF$_3$, CH$_2$OR$^4$, COR$^4$, CONR$^4$R$^4$, CO$_2$R$^4$, CN, phenyl optionally substituted by one to three moieties selected from the group consisting of C$_{1-4}$alkyl, C$_{1-4}$alkoxy, C$_{1-4}$alkthio, trifluoroalkyl, OH, F, Cl, Br, and I, naphtyl optionally substituted by one to three moieties selected from the group consisting of C$_{1-4}$alkyl, C$_{1-4}$alkoxy, C$_{1-4}$alkthio, trifluoroalkyl, OH, F, Cl, Br, and I, an optionally substituted five or six membered aromatic monocyclic ring, a nine or ten-membered bicyclic ring containing one to three heteroatoms chosen from the group consisting of nitrogen, oxygen and sulfur, NR$^4$R$^4$, NR$^4$COR$^4$, NR$^4$CO$_2$R$^4$, NR$^4$CONR$^4$R$^4$, NR$^4$SO$_2$R$^4$, NO$_2$, OR$^4$, S(O)$_{0-2}$R$^4$, or SO$_{(0-2)}$CF$_3$;

$R^1$ is —(CH$_2$)$_m$COR$^3$;

$R^2$ is —(CH$_2$)$_q$COR$^3$;

R* is

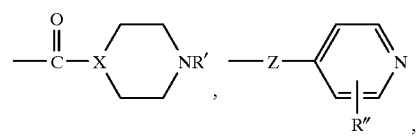

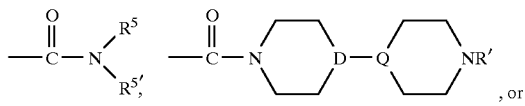
, or

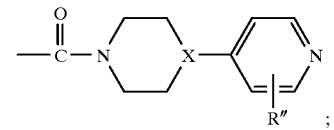
;

$R^3$ is OR' or NR'R';

$R^4$ is hydrogen, C$_{1-6}$alkyl, aralkylC$_{1-6}$, phenyl optionally substituted by one to three moieties selected from the group consisting of C$_{1-4}$alkl, C$_{1-4}$alkoxy, C$_{1-4}$alkthio, trifluoroalkyl, OH, F, Cl, Br, and I, naphtyl optionally substituted by one to three moieties selected from the group consisting of C$_{1-4}$alkyl, C$_{1-4}$alkoxy, C$_{1-4}$alkthio, trifluoroalkyl, OH, F, Cl, Br, and I, heteroaralkylC$_{1-6}$, or an optionally substituted five or six membered aromatic monocyclic ring, a nine or ten-membered bicyclic ring containing one to three heteroatoms chosen from the group consisting of nitrogen, oxygen and sulfur;

each R' independently is hydrogen or C$_{1-6}$alkyl;

R'' is hydrogen, C$_{1-6}$alkyl, or NR'R';

D and Q independently are CH or N, with the proviso that D and Q are not simultaneously N;

X is CH or N;
Z is C(O)NR' or NR'C(O);
$R^5$ and $R^{5'}$ independently are $-(CH_2)_s-Ⓝ$;
Ⓝ is piperidine, piperazine, or 2-, 3-, or 4-pyridine;
m is 0–3;
n is 0–3;
each q independently is 1–3; and
s is 1–4;
or a pharmaceutically acceptable salt thereof.

2. A compound according to claim 1 wherein R* is

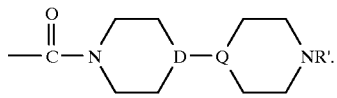

3. A compound according to claim 2 wherein $R^3$ is OR', D and Q are each CH, and n is 1 or 2.

4. A compound according to claim 3 which is:

1-[4,4'-bipiperidin-1-yl]isophthalyl-4-piperidine carboxylic acid;

(+)-1-[4,4'-bipiperidin-1-yl]isophthalyl-3-piperidine carboxylic acid;

1-[4,4'-bipiperidin-1-yl]terephthalyl-4-piperidine carboxylic acid; or (+)-1-[4,4'-bipiperidin-1-yl]terephthalyl-3-piperidine carboxylic acid; or pharmaceutically acceptable salts thereof.

5. A pharmaceutical composition comprising a compound according to claim 1 and a pharmaceutically acceptable carrier.

6. A method for effecting inhibition of platelet aggregation which comprises administering a fibrinogen receptor binding inhibitory effective amount of a compound according to claim 1.

* * * * *